United States Patent [19]

Gralnick

[11] Patent Number: 5,366,865
[45] Date of Patent: Nov. 22, 1994

[54] ANTI-PLATELET MONOCLONAL ANTIBODY

[75] Inventor: Harvey R. Gralnick, Kensington, Md.

[73] Assignee: The United States of America as represented by the Secretary of the Department of Health and Human Services, Washington, D.C.

[21] Appl. No.: 334,708

[22] Filed: Apr. 6, 1989

[51] Int. Cl.⁵ .................. G01N 33/574; G01N 33/53; C12N 5/12; C07K 15/28
[52] U.S. Cl. ..................... 435/7.23; 435/7.1; 435/240.27; 530/388.22; 530/388.25
[58] Field of Search .................. 435/240.27, 7.1, 7.23; 530/387, 388, 388.22, 388.25; 935/104, 100, 110, 108

[56] References Cited

PUBLICATIONS

Giltay, J. C., Blood, 73(5):1235–1241, Apr. 1989.
Pischel, K. D., J. Clin Invest, 81:505–513, Feb. 1988.
Coller, et al., Clinical Research, 36(3):563A, 1988 (Abstract).
Staatz, et al., J. Cell. Biol. 108:1917–1924, May 1989.
McGregor et al., Eur. J. Biochem., 131:427–436, 1983.
Coller et al., Blood, 74(1):182–192, Jul. 1989.

Primary Examiner—David L. Lacey
Assistant Examiner—Susan A. Loring
Attorney, Agent, or Firm—Birch, Stewart Kolasch & Birch

[57] ABSTRACT

A method for producing novel monoclonal antibodies against purified platelets are provided. A monoclonal antibodies which inhibits platelet reactions with collagen or collagenous surfaces is described. A new method of detecting and treating tumor metastatis is described.

6 Claims, 5 Drawing Sheets

FIG. 2

PLATELET ADHESION TO SUBENDOTHELIUM

| Patient | Amount of Antibody 176D7 added μg/ml | Contact % | Spread % | C&S % |
|---|---|---|---|---|
| 1. | 10 | -8 | -30 | -29 |
|  | 20 | +14 | -56 | -53 |
| 2. | 10 | -36 | -27 | -27 |
|  | 20 | -7 | -58 | -56 |
| 3. | 10 | -8 | -39 | -38 |
|  | 20 | +17 | -41 | -39 |
| 4. | 10 | -38 | -39 | -38 |
|  | 20 | -61 | -69 | -69 |
| Mean | 10 | -23 | -34 | -33 |
|  | 20 | -17 | -56 | -54 |

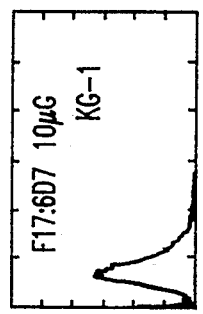
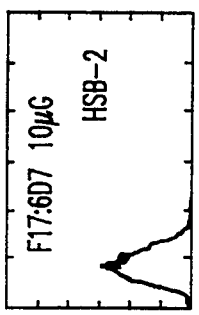
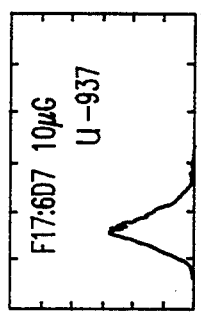
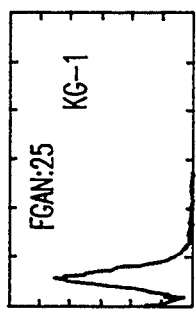
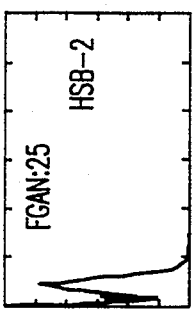
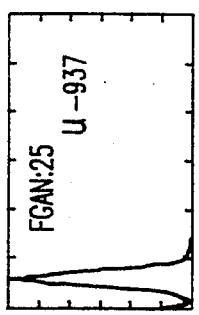
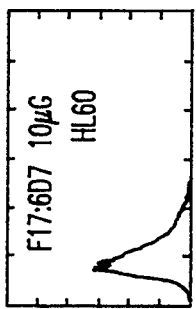
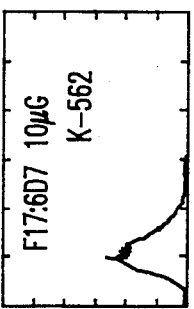
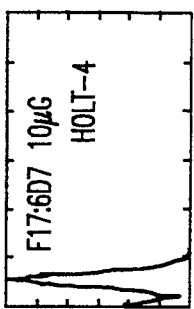
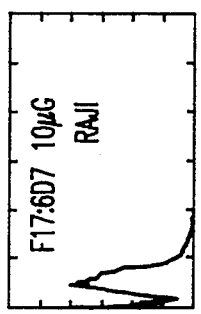
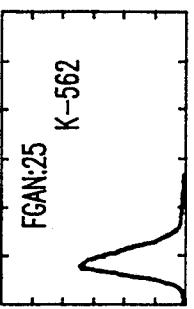
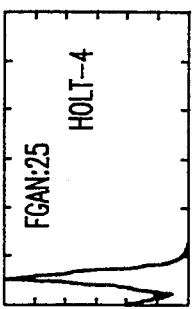
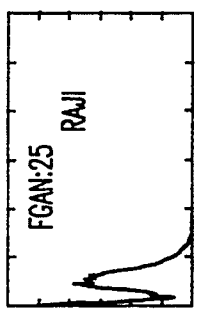

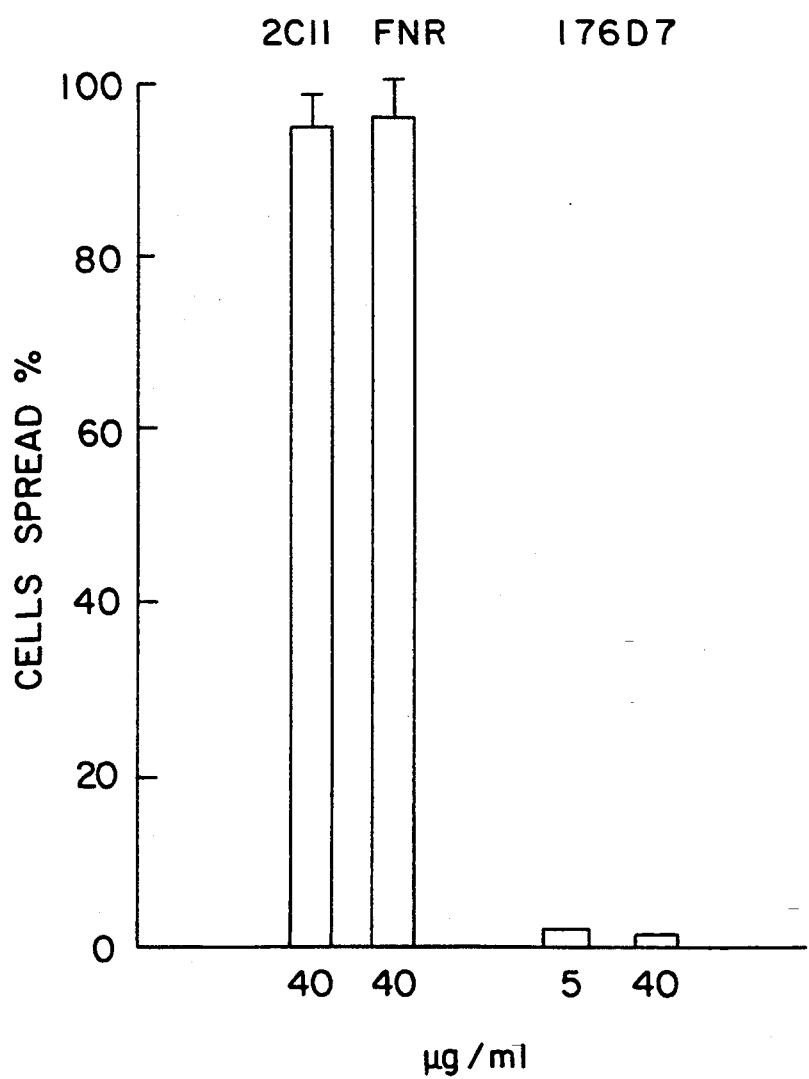

ANTI-PLATELET MONOCLONAL ANTIBODY

The present invention is related generally to the preparation of monoclonal antibodies. More particularly, the present invention is related to providing anti-platelet monoclonal antibodies which recognize a specific heterodimer antigen, composed of two components with molecular weights of about 157 and 130 kDa. Such an antibody, designated herein as 176D7, has not heretofore been known or described.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 demonstrates the inhibition of platelet adhesion to subendothelium by antibody 176D7. The antibody at the concentrations of 10 or 20 μg/ml was added to whole blood prior to the perfusion over an umbilical artery segment from which the endothelial cells had been removed. In four subjects the monoclonal antibody inhibited both contact and spreading of platelets on the subendothelial surface. At 20 μg/ml the decrease was 54 percent. Each individual served as their own control to which a monoclonal antibody 2C11 had been added.

FIGS. 4A–4N further demonstrates flow cytometric identification of F1767 antigen on tumor cells. The cells from a human promyelocytic leukemia line (HL-60) are positive. Cells from acute myelogenous leukemia cell line (KG-1), cells from a chronic myelogenous leukemia line (KG-1) and cells from a monocytehistiocyte like lymphoma line (V937) are all positive. The cell lines Molt 4 and Raji both of lymphocyte tumor origin are negative.

FIG. 5 demonstrates the inhibition of spreading of tumor cells on a collagen gel. Human fibrosarcoma cells from a long term culture were incubated with a collagen gel in the presence and absence of monoclonal antibody. Cell spreading was determined by inverted and phase microscopy. The control antibody added is 2C11 which does not inhibit the tumor cell spreading on gel. The αfibronectin receptor antibody (αFNR) also does not inhibit spreading of these cells on collagen. The anticollagen receptor antibody, 1767 (aCR) in doses of 5 and 40 μg/ml totally inhibited the spreading of tumor cells on collagen.

MATERIALS AND METHODS

Figure 1:
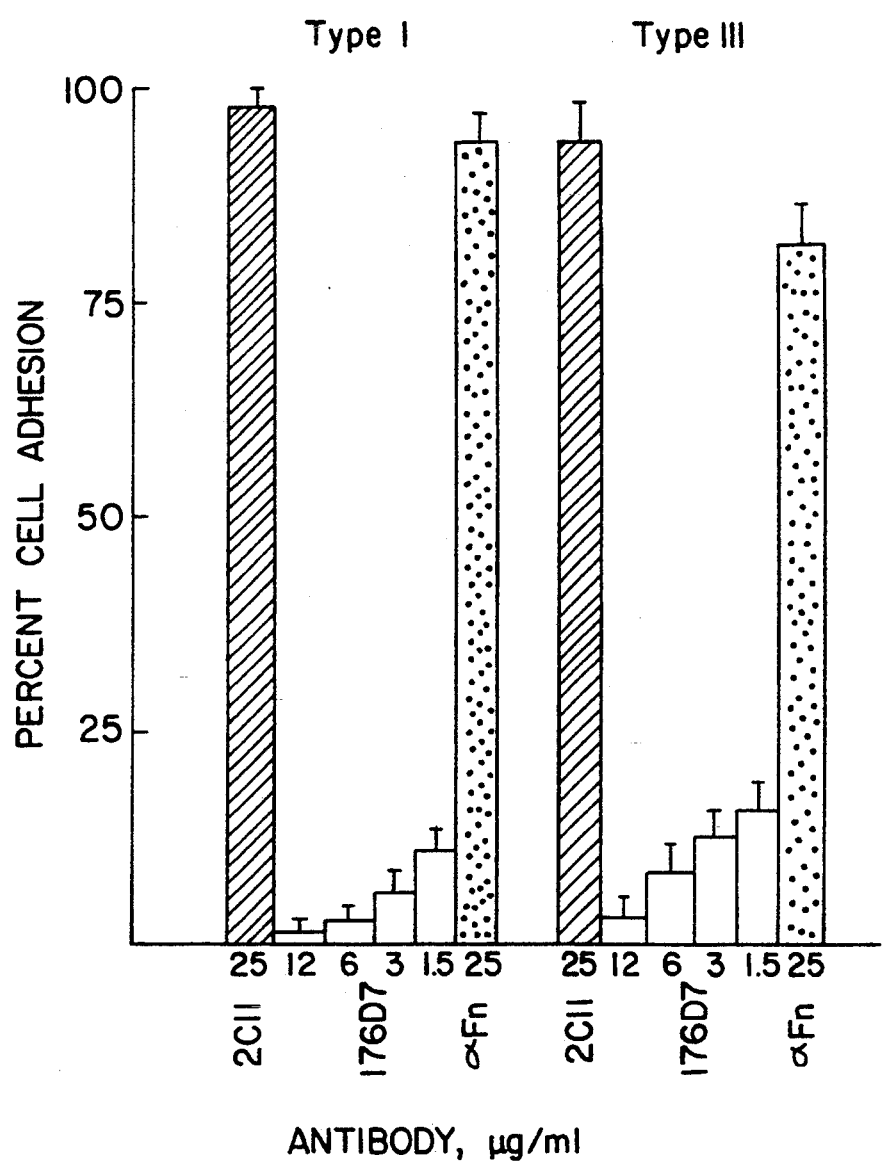
FIG. 1 shows the effect of the antibody of the present invention on platelet adhesion. Concentrations of 1767 ranging from 12 to 1.5 μg/ml were added to platelets prior to their addition to collagen coated microtiter plates. The antibody 1767 showed complete inhibition of adhesion at a dose of 12 μg/ml and at a dose of 1.5 μg/ml there was still significant inhibition. Antibody 2C11 is a control monoclonal antibody and αFn antibody is an antifibronectin receptor antibody which did not inhibit platelet adhesion to collagen. The results of the type I and type III collagen are almost identical.
Figure 3A:
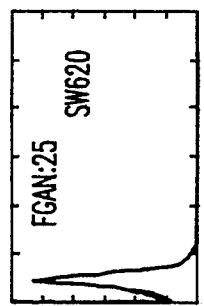
FIGS. 3A–3D shows flow cytometric identification of the F1767 antigen on tumor cells. The antibody of 1767 was incubated with a variety of tumor cells from long term cultures. The cells were washed and fluorescence was detected by the addition of FITC goat antimouse antibody. For each of the cell lines there is a control. The FGAM:25 is the addition of the FITC labeled goat antimouse antisera to the cells in the absence of the 1767. To the right of each of these is the result when F1767 has been added prior to the addition of the FGAM:25. The cells that tested positive include: cells from human colon carcinoma, human lung carcinoma (A-427), human melanoma cells (MT-144, SKMEL-28), human breast adenocarcinoma cells (BT-20) but there is no reaction with cells from an osteosarcoma cell line, SA052.
Figure 3B:
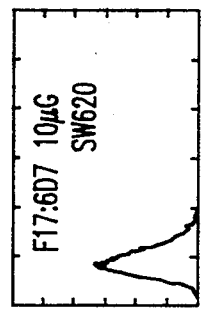
Figure 3C:
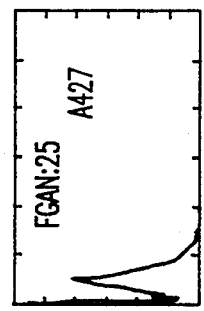
Figure 3D:
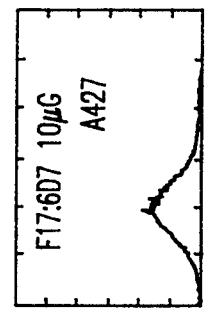
Figure 3E:
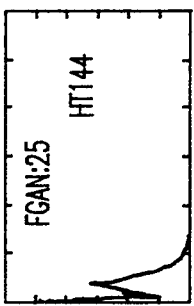
Figure 3F:
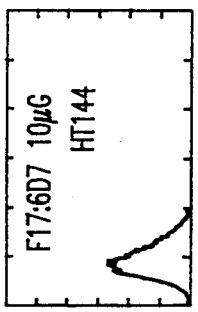
Figure 3G:
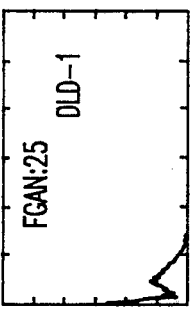
Figure 3H:
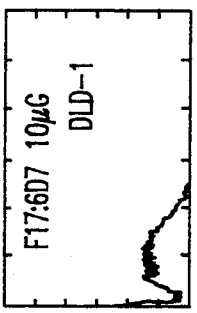
Figure 3I:
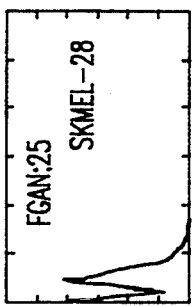
Figure 3J:
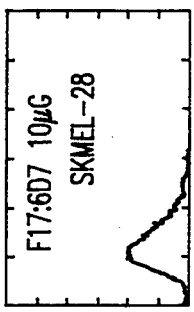
Figure 3K:
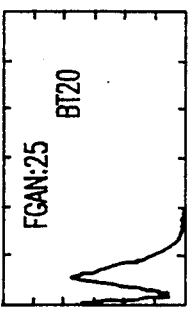
Figure 3L:
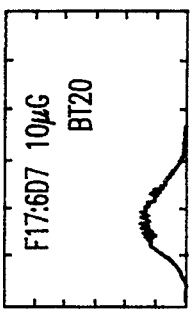
Figure 3M:
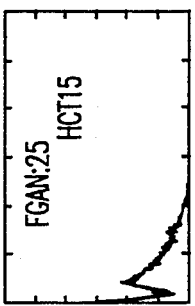
Figure 3N:
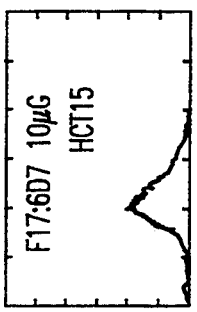
Figure 3O:
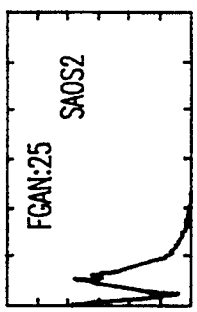
Figure 3P:
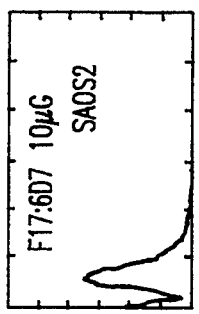

The following are only illustrative and not limiting.
Platelet Aggregation and Release Reaction Aggregation of platelets in PRP (platelet rich plasma) is measured on an aggregometer, an instrument that measures increases in light transmission through a cuvette of stirred PRP. Various agents (epinephrine, ADP, ristocetin, collagen and the like) are added to the PRP to cause aggregation and change in the optical density as an index of platelet aggregation is recorded on a graph.

Following aggregation, platelets release specific chemical substances (ADP, ATP, Serotonin, calcium ions and the like). The secretion of ATP is measured by detecting the luminescence in the firefly luciferase system.

Reagents and Material:
1. Lumi-Aggregometer and recorder.
2. Glass cuvettes (Chrono-Log Corp.) siliconized in 1% silicon solution (Prosil-28 PCR Research Chemicals, Inc.).
3. Teflon coated stir bars (Chrono-Log Corp.).
4. Plastic pipettes and tubes.
5. Device for maintaining pH and controlling humidity (Coller et al: The pH Dependence of Quantitative Ristocetin-induced Platelet Aggregation: Theoretical and Practical Implication-A New Device for Maintenance of Platelet Rich Plasma pH. BLOOD 47:841, 1976).
6. Epinephrine (Park-Davis Co.) MW183.2. Working solution 0.68 mM. Dilute 1.0 ml from a liquid ampule (1 mg/ml) 1:8 with 0.15M NaCl. Aliquot to 1.0 ml and store at −70° C. Thaw fresh sample daily.
7. ADP (Adenosine 5' Diphosphate Disodium) (Sigma Co.) MW427.2 Stock solution 0.225 mM. Dilute 9.6 mg to 100 ml in 0.15M NaCl, aliquot to 2 ml and store at −70°. Thaw fresh sample daily before use. Dilute stock solution 1:2.5 (.090 mM) and 1:5 (0.045 mM) with 0.15M NaCl for working solutions.
8. Soluble Collagen (Worthington Biochemical Corp.) 7.0 mg/ml protein. Store in the cold and when using, keep on ice. Tendrils form at room temperature.
9. Ristocetin Sulphate (Lenau, Copenhagen, Denmark) Working solution of 80 mg/ml, 60 mg/ml, 40 mg/ml and 20 mg/ml are diluted in 0.01M Tris-0.15M NaCl pH 7.4. Store at room temperature (about 22°–24° C.).

10. Thrombin (purified Human thrombin) Stock solution 100 U/ml diluted in 0.01M Tris-0.15M NaCl-0.66% PEG 6000 pH 7.35. Store at −70° C. Thaw fresh sample daily and dilute to 1.5 & 2.0 U/ml with 0.01M Tris-0.15M NaCl pH 7.35.

11. Luciferace (Sigma) Store powder at −70° C. Working solution 40 mg/ml diluted in distilled water. Make fresh daily, protect from light and keep on ice.

12. ATP (Adenosine 5'-Triphosphate, Disodium salt from Equine Muscle) (Sigma Co.) MW551.2 Working solution 0.34 mM. Dissolve 18.6 mg ATP in 100 ml NaCl. Aliquot to 2 ml and store at −70° C. Thaw fresh sample daily. Final concentration 1.5 µM.

Procedure:

Draw 20 cc blood in 38% Na Citrate (0.1 ml/10 ml blood) with a 29 guage needle using a two-syringe technique. Perform a platelet count on whole blood and keep at room temperature.

Prepare Platelet Rich Plasma (PRP) by spinning the Whole Blood at 750 g, 3 min. Spin the remainder of the whole blood at 2,000 g for 10–15 minutes at 24° C. The plasma is now platelet poor. Save 0.4 ml for a blank before adjusting the PRP to 2,000,000/mm.

Adjust pH of PRP at 200,000/mm to pH 7.7 (±.05). If the pH is too high, add a small amount of $CO_2$ to the PRP. If the pH is too low, mix the PRP gently between two plastic tubes.

Aliquot 0.4 ml PRP into siliconized cuvettes and place in a device to control pH and humidity. The pH of the platelets will be stable for about 6 hours.

Set up the aggregometer according to the instruction manual; allow PRP to run for 1 minute without more than a 0.2 unit change. Also record each aggregation until the OD changes less than 0.2 units/minute.

When the PRP has stabilized, add 50 Luciferase. After 1 minute add epinephrine, ADP, ristocetin, thrombin or collagen. Avoid bubbles which will cause the pen to become very erratic. The first wave of aggregation indicates direct contact of reagent on platelets. The second wave indicates release of endogenous ADP which will cause the remaining free platelets to clump. Platelets lose their sensitivity to epinephrine and ADP about 3 hours after drawing. If the patient is abnormal, increase or decrease the amount of reagent in an attempt to produce a normal curve. At the end of the aggregation and release response add 2 ATP(.34 mM) in order to measure the amount of ATP released from the platelet. Calculate the % yield of the control and patient:

$$\frac{\text{Total number platelets in Whole Blood}}{\text{Total number platelets in PRP}} = \% \text{ yield}$$

To test for platelet sensitivity to heparin add 20 of the patient's heparin (40 units/ml) to 0.4 ml PRP (control and patient). Record platelet activity for 10 minutes. Next, add 50 of the patient's PPP to 0.4 ml of the control PRP, allow to stabilize for 1 minute and add 20 heparin (40 units/ml). Record platelet activity for 10 minutes. Final Concentration of reagents

|    |             | Working Solution | Final Concentration |
|----|-------------|------------------|---------------------|
| 5  | Epinephrine | 0.68 mM          | 7.5 µM              |
| 20 | ADP         | 0.045 mM         | 1.9 µM              |
|    |             | 0.090 mM         | 3.8 µgM/ml          |
| 15 | Collagen    | 7 mg/ml          | 226 µgM/ml          |
| 10 | Ristocetin  | 80 mg/ml         | 1.74 mg/ml          |
|    |             | 60 mg/ml         | 1.30 mg/ml          |
|    |             | 40 mg/ml         | 0.87 mg/ml          |
|    |             | 20 mg/ml         | 0.44 mg/ml          |
| 50 | Thrombin    | 1.5 U/ml         | 0.15 U/ml           |
|    |             | 2.0 U/ml         | 0.20 U/ml           |

| Reagents | Normal Results Aggregation |
|----------|---------------------------|
| Epinephrine | Double Wave |
| ADP | Large single wave or double wave |
| Collagen | Single wave lag time 1–3 min. |
| Thrombin | Single wave or double wave |
| Ristocetin | Double wave or single wave |

Preparation of Monoclonal Antibodies:

The antibody, 176D7, was prepared against purified platelets isolated from whole blood by standard procedures using Stractan (arabinogalactan) gradients and injected into mice. The third injection into mice was an intrasplenic injection. Hybridomas were prepared by standard techniques and the multiple clones formed were tested for their ability to inhibit collagen-induced platelet aggregation by the methodology described herein supra, and a hybridoma secreting antibody 176D7, which showed desirable properties, was selected. This hybridoma was deposited with the American Type Culture Collection, 12301 Parklawn Drive, Rockville, MD 20852-1776, on Feb. 7, 1992 under the accession number ATCC HB 10973. It is noted that antibody 176D7 did not interfere with the aggregation of platelets by any other agonist. This antibody specifically inhibits the adhesion of platelets to type I and III collagen in a dose-dependent fashion in the presence of $Mg^{++}$ and blocks platelet interaction with collagen surface and inhibits it at concentrations as low as 1 microgram per ml final concentration (FIG. 1). It has no effect on adhesion of platelets to fibronectin or von Willebrand factor. In addition to inhibiting the adhesion to matrix, it also inhibits collagen-induced platelet aggregation of both purified platelets and platelet-rich plasma. It binds to about 1,900±300 sites per platelet with a Kd of about 5 nM. Binding of the antibody to the platelets of 11 normal subjects gave a Kd of about 5.1±1.2 nM and the number of sites per platelet was found to be about $1.9 \pm 0.16 \times 10^3$. Antibody 176D7 also inhibits the adhesion of platelets to the subendothelium of umbilical arteries, in a flowing system (Baumgartner technique). This technique involves perfusing whole blood at flow rates (sheer forces) found in the microvasculature; that is a sheer force of approximately 2600 inverse seconds (FIG. 2).

The antibody 176D7 immunoprecipitates a 157/130 kDA heterodimeric antigen from the platelet surface. In the non-reduced state, this heterodimer has molecular weights of approximately 136 for the alpha subunit and 105 for the beta subunit. After reduction of the disulfide bonds, the alpha subunit increases in molecular size to about 156 kDa and the beta subunit increases in molecular size to about 130 kDa. The role of this antibody is quite important in thrombosis, vessel wall growth, cancer growth and metastasis of cancer.

Antibody 176D7 binds to purified platelets without exogenous proteins and to platelets in the presence of plasma proteins. The association constant is identical in the presence or absence of plasma proteins, however, the number of binding sites per platelet is decreased approximately 15% in the presence of plasma proteins. This monoclonal antibody also recognizes the a collagen receptor present on endothelial cells, on tissue culture lines which include breast cancer cells, lung cancer cells, melanoma cells, colon cancer cells (FIGS. 3 and 4). Tests indicate that this antibody also inhibits the spreading and migration of fibrosarcoma cells on a collagen surface (FIG. 5).

Antibody 176D7, which recognizes a collagen receptor, is also able to totally inhibit all aspects of collagen-platelet interactions. In particular, it inhibits the adhesion of platelets to collagen surfaces, the aggregation of platelets in the presence or absence of plasma proteins to collagen, and inhibits the binding of platelets in a flowing system to the vessel subendothelium (FIG. 2). The antibody recognizes a specific antigen found on human platelets, human endothelial cells, and a wide variety of human tumor cells (FIGS. 3 and 4).

The antibody of the present invention is quite useful in detecting tumor cells which contain the heterodimeric antigen mentioned above. The data indicate that, in the presence of this antibody, tumor cells are inhibited from migrating onto a collagen surface (FIG. 5). Since collagen plays a pivotal role in the ability of cancer cells to metastasize, the collagen inhibiting property of 176D7 makes it useful as an inhibitor of tumor cell metastasis by inhibiting the interaction of tumor cells with a collagen substrate. For the same reason, 176D7 is also useful in the treatment of patients who have cardiovascular disease with angina pectoris or acute myocardial infarction due to rupture of an atherosclerotic plaque. In these conditions, collagen is exposed in the subendothelium and as demonstrated herein this antibody would inhibit platelet interaction with collagen which, in turn, prevents the formation of new thrombus which might partially or totally occlude the vessel.

A diagnostic kit comprising a container containing the antibodies 176D7 of the present invention now makes it possible to identify tumor cells from biopsies or other tissues and to ascertain whether the tumor cells contain the surface glycoprotein specifically recognized by 176D7. The kit also allows the diagnosis of specific platelet defects, both congenital and acquired, involving the collagen receptor on platelets. These tests are performed by routine immunological, cytological or hematological techniques and the like, such as antibody binding, immunofluorescence, flow cytometry and the like, well known to one of ordinary skill in the art.

The antibodies of the present invention also allow the determination in experimental animals whether, in the presence of the antibody, injected tumor cells or tumor cells inoculated into an organ, metastasize or if metastasis is inhibited. This would also allow the determination of whether the metastasis occurred through the interaction of glycoprotein Ia/IIa on the tumor cell surface with collagen. Inhibition of this interaction by 176D7 would result in decreased number of individual cells metastasizing, growing and forming tumor nodules. This would be significant in the formulation of therapeutic modalities in the treatment of metastasis in cancer.

A composition comprises the monoclonal antibodies 176D7 in an effective amount to inhibit platelet reactions with collagenous surfaces and pharmaceutically acceptable vehicle.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. The hybridoma deposited as ATCC HB 10973 secreting monoclonal antibody 176D7, said monoclonal antibody having the following properties:
   (a) recognizes a 157/130 kDa heterodimeric antigen of platelet and surfaces
   (b) inhibits platelet reactions with collagenous surfaces, adhesion to type I and type III collagen and collagen induced platelet aggregation even in the presence of plasma.

2. Monoclonal antibody, 176D7, produced by the hybridoma ATCC HB 10973 properties:
   (a) recognizes a 157/130 kDa heterodimeric antigen; and
   (b) inhibits platelet reactions with collagenous surfaces, adhesion to type I and type III collagen and collagen induced platelet aggregation even in the presence of plasma.

3. A diagnostic kit, comprising a container containing antibody 176D7 produced by the hybridoma ATCC HB 10973.

4. A method for determining the presence of a 157/130 kDa heterodimeric antigen or platelet surfaces, comprising the steps of reacting a biological sample suspected of having said antigen with the monoclonal antibody of claim 2 and determining a binding reaction between said antigen and said antibody, the occurrence of antigen-antibody reaction being indicative of the presence of said antigen in said sample.

5. A method for detecting the presence of a heterodimeric collagen receptor, composed of 157 kDa and 130 kDa subunits, on the surface of cells, comprising the steps of:
   1) contacting cells suspected of expressing said collagen receptor with the antibody of claim 2, under conditions favorable for binding of said antibody to said antigen,
   2) detecting the binding of said antibody to the surface of said cells,
   a positive result in step (2) being indicative of the presence of said collagen receptor on the surface of the cell.

6. A method according to claim 8, wherein the detection step (2) is performed using a fluorescent-labelled antimouse antibody.

* * * * *